(12) United States Patent
Adams et al.

(10) Patent No.: US 7,270,651 B2
(45) Date of Patent: Sep. 18, 2007

(54) ABSORBENT ARTICLE

(75) Inventors: Dannette ReNee Adams, Independence, KY (US); Forrest Timothy Maloney, Mason, OH (US); Patricia Lee Christon, Cincinnati, OH (US); Bryan Keith Feller, Wyoming, OH (US); Ronda Lynn Glassmeyer, Cincinnati, OH (US); Rosa Alejandra Hernandez, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 361 days.

(21) Appl. No.: 10/967,454

(22) Filed: Oct. 18, 2004

(65) Prior Publication Data

US 2005/0124954 A1   Jun. 9, 2005

Related U.S. Application Data

(63) Continuation-in-part of application No. 10/945,403, filed on Sep. 20, 2004, which is a continuation of application No. 10/796,883, filed on Mar. 9, 2004, now Pat. No. 7,163,528, which is a continuation of application No. 10/025,059, filed on Dec. 19, 2001.

(51) Int. Cl.
*A61F 13/15* (2006.01)
*A61F 13/20* (2006.01)

(52) U.S. Cl. .................. 604/385.01; 604/378
(58) Field of Classification Search ................ 604/359, 604/361–362, 367, 378, 385.01, 381
See application file for complete search history.

(56) References Cited

U.S. PATENT DOCUMENTS

| | | |
|---|---|---|
| 2,881,761 A | 4/1959 | Kenner |
| 4,623,340 A | 11/1986 | Luceri |
| 4,908,026 A | 3/1990 | Sukiennik |
| 4,909,879 A | 3/1990 | Ball |
| 5,006,394 A | 4/1991 | Baird |
| 5,188,625 A | 2/1993 | Vaniten |
| 5,261,899 A | 11/1993 | Visscher |
| H1376 H * | 11/1994 | Osborn et al. ............... 604/361 |
| 5,401,267 A | 3/1995 | Couture-Dorschner |
| 5,437,653 A | 8/1995 | Gilman |
| 5,454,800 A | 10/1995 | Hirt |
| 5,458,590 A | 10/1995 | Schleinz |
| 5,503,076 A | 4/1996 | Yeo |
| 5,562,037 A | 10/1996 | Schleinz |

(Continued)

FOREIGN PATENT DOCUMENTS

EP    0 605 730 A1    7/1994

(Continued)

*Primary Examiner*—Michele Kidwell
(74) *Attorney, Agent, or Firm*—Amanda T. Barry; Roddy M. Bullock; David M. Weirich (57) ABSTRACT

The absorbent article provides a signal viewable from the top surface of the absorbent article which gives a perception of depth within the absorbent article. This creation of depth perception is accomplished by the use of at least two tones within a color and/or by the use of multiple tones and multiple colors operating together to create a perception of depth within the absorbent article. At least one tone contains a graphic.

15 Claims, 6 Drawing Sheets

U.S. PATENT DOCUMENTS

| | | | |
|---|---|---|---|
| 5,566,616 A | 10/1996 | Schleinz | |
| 5,683,752 A | 11/1997 | Popp | |
| 5,766,389 A | 6/1998 | Brandon | |
| 5,818,719 A | 10/1998 | Brandon | |
| 5,897,541 A | 4/1999 | Uitenbrock | |
| 6,075,178 A | 6/2000 | LaWilhelm | |
| 6,264,640 B1 | 7/2001 | Sutton | |
| 6,297,424 B1 * | 10/2001 | Olson et al. | 604/361 |

FOREIGN PATENT DOCUMENTS

| | | |
|---|---|---|
| EP | 0 774 946 B1 | 5/1997 |
| EP | 0 794 280 A2 | 9/1997 |
| EP | 0 951 889 A1 | 10/1999 |
| EP | 1 057 465 A1 | 12/2000 |
| EP | 1 199 057 A1 | 4/2002 |
| EP | 1 203 571 A2 | 5/2002 |
| GB | 1070514 | 6/1967 |
| WO | WO 94/26221 A1 | 11/1994 |
| WO | WO 96/10380 A2 | 4/1996 |
| WO | WO 99/56690 A1 | 11/1999 |
| WO | WO 00/38915 A1 | 7/2000 |
| WO | WO 01/32318 A2 | 5/2001 |

* cited by examiner

ABSORBENT ARTICLE

CROSS REFERENCE TO RELATED APPLICATIONS

This application is continuation-in-part of U.S. application Ser. No. 10/945,403, filed Sep. 20, 2004, pending, which was a continuation of U.S. application Ser. No. 10/796,883, filed Mar. 9, 2004 now U.S. Pat. No. 7,163,528, which was a continuation of U.S. application Ser. No. 10/025,059, filed Dec. 19, 2001 pending.

FIELD OF THE INVENTION

The invention provides an absorbent article having a multi-tone signal of at least one color having a graphic. The effect of the multi-tone signal creates a perception of depth by a user viewing the topsheet surface of the absorbent article.

BACKGROUND OF THE INVENTION

Printing on or below the top surface of an absorbent article is known in the art. Printing to create a signal that masks stains is also known. Overcoming the problem of unsightly stains during, for example, a woman's menstrual period has been disclosed. What has not been disclosed or taught is the use of multi-toned printing to create a signal that provides a perception of depth to an absorbent article when the article is viewed from its top or viewing surface. By creating a perception of depth within the absorbent article a user is reassured prior to use and during use that fluid will be drawn deep inside the product and away from a user's body.

Through the use of innovative topsheet materials, secondary topsheet materials, absorbent gelling materials and breathable backsheets, the technology in absorbent articles, and particularly sanitary napkins, has drastically advanced to provide women with more than adequate, if not excellent, products that absorb menses and other fluids away from a woman's body. However, much of this technology is often hidden and therefore not viewable. When seen, absorbent components often do not readily or visually communicate to a user the existence of this enhanced technology.

The ability to communicate to a consumer the existence of enhanced functioning of an absorbent article is a premium asset to any absorbent article. Hence, the use of the multi-toned signals has been created to begin to address the problem of such communication. This is especially so since mostly all of the products on the market today have as their main function the objective to mask menses rather than conveying the product's enhanced functioning power. The art is replete with examples of the use of a one-tone signal for such masking.

Communicating enhanced functioning characteristics by creating the perception of depth within an absorbent article is one unique and novel way to solve this problem, that prior to this reduction to practice has not been taught, suggested or disclosed by the prior art. Using multiple tones (i.e., at least two) of a color and/or multiple tones and multiple colors together to create a perception of depth can engender in a user the perceived belief of better protection and enhanced functioning by creating the perception of depth once a user has viewed the multi-tone configuration from the viewing surface of the absorbent article, such perception continuing through and after wear of the absorbent article.

SUMMARY OF THE INVENTION

Accordingly, the invention provides an absorbent article having an upper surface, a lower surface and a periphery comprising a topsheet having a bottom surface and a viewing surface positioned opposite to the bottom surface. The viewing surface faces upwardly towards the upper surface of the absorbent article. The absorbent article further comprises a backsheet having a garment facing surface and a user facing surface positioned oppositely to the garment facing surface, the backsheet being joined to the topsheet.

An absorbent core having a top surface and a bottom surface that is positioned opposite to the top surface. The absorbent core is positioned between the topsheet and the backsheet. The viewing surface of the absorbent article preferably, but not necessarily, has at least two portions, i.e., a colored portion and a non-colored portion. The colored portion and the non-colored portion are viewable from the viewing surface of the topsheet. The colored portion has at least two shades, a first shade and a second shade. The first shade is positioned substantially within the second shade. The second shade is different, either in lightness, darkness, and/or color, from the first shade. The multi-shades operate to create a perception of depth within the absorbent article by a user looking upon the viewing surface of the topsheet. In one embodiment herein, the first shade of the color is darker than the second shade of the color. Alternatively, the first shade is lighter than the second shade.

In one embodiment, the first shade comprises a first graphic. In yet another embodiment, the second shade comprises a second graphic. Moreover, in yet another embodiment the first shade comprises a first graphic and the second shade comprises a second graphic.

The color of the first shade and the second shade of the colored portion and the non-colored portion are measured by reflectance spectrophotometer ASTM standard test methodology. Tristimulus $L^*$, $a^*$, $b^*$ values are measured from the viewing surface of the topsheet inboard of the absorbent article's periphery. These $L^*$, $a^*$, $b^*$ values are reported in terms of the CIE 1976 color coordinate standard The color differences between the colored portion and the non-colored portion are measured at a first point, a second point, and a third point on the viewing surface of the topsheet inboard of the periphery of the absorbent article. Preferably, each one of the points noted (i.e., 1, 2 and 3) resides fully within the periphery of the absorbent core. For example, the first point is measured within the first shade, the second point is measured within the second shade, and the third point is measured within the non-colored portion of the absorbent article. The color differences are calculated according to method ASTM D2244-99 "Standard Test Method for Calculation of Color Differences from Instrumentally Measured Color Coordinates."

The difference in color (i.e., $\Delta E^*$) between the first shade and the second shade should be at least 3.5. The $\Delta E^*$ is calculated by the formula $\Delta E^* = [(L^*_X - L^*_Y)^2 + (a^*_X - a^*_Y)^2 + (b^*_X - b^*_Y)^2]^{1/2}$. X may represent points 1, 2 or 3. Y may represent points 1, 2 or 3. X and Y should never be the same two points of measurement at the same time. In other words, $X \neq Y$. The difference in color between the first shade and the non-colored portion is at least 6. The difference in color between the second shade and the non-colored portion is at least 3.5. Preferably, the size of the colored portion ranges from about 5% to about 100% of the viewing surface of the topsheet. Also preferably, the first shade of the colored portion is positioned substantially centrally in relation to the second shade of the colored portion. However, so long as the shades are in proper spatial relationship to one-another such that the depth perception phenomena is created, any suitable positioning of the shades is suitable and foreseeable by one of skill in the art and are therefore acknowledged as suitable alternative embodiments of the invention.

In one embodiment herein, the colored portion may be an insert positioned between the topsheet and the absorbent core. In another embodiment, the colored portion forms a part of the topsheet. In yet another embodiment herein, the colored portion forms a part of the absorbent core whereby the colored portion is viewable from the viewing surface of the topsheet. Alternatively, the colored portion may be a multi-layered insert positioned beneath the topsheet.

Any topsheet material that allows the colored portion to be readily seen from the viewing surface of the topsheet is suitable. For example, formed film material, nonwovens, other topsheet materials known in the art or combinations thereof are suitable.

In an alternative embodiment herein, the absorbent article provides a colored portion and is substantially without a non-colored portion. The colored portion is viewable from the viewing surface of the topsheet and has at least two shades, a first shade and a second shade. The first shade is positioned substantially within the second shade, the second shade being different from the first shade. The at least two shades operate to create a perception of depth within the absorbent article by a user looking upon the viewing surface of the topsheet.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Section A will provide terms which will assist the reader in best understanding the features of the invention but not to introduce limitations in the terms inconsistent with the context in which they are used in this specification. These definitions are not intended to be limiting. Section B will discuss the sanitary napkin of the present invention. Section C will discuss them methods.

A. Terms

"Absorbent articles" as referred to herein are primarily sanitary napkins, pantiliners, or incontinence pads that are worn in the crotch region of an undergarment. It is even conceivable that baby diapers, adult incontinence diapers, and human waste management devices benefit from the present invention even though they are conventionally not worn in conjunction with an undergarment.

The term "color" as referred to herein include any primary color, i.e., white, black, red, blue, violet, orange, yellow, green, and indigo as well as any declination thereof or mixture thereof. The term 'non-color' or 'non-colored' refers to the color white which is further defined as those colors having an L* value of at least 90, an a* value equal to 0±2, and a b* value equal to 0±2.

The term "disposable" is used herein to describe absorbent articles that are not intended to be launched or otherwise restored or reused as absorbent articles (i.e., they are intended to be discarded after a single use and, preferably to be recycled, composted or otherwise disposed of in an environmentally compatible manner).

B. Sanitary Napkin of the Present Invention

Non-limiting examples of panty liners and sanitary napkins which may be provided with a multi-tone signal that operates to create depth perception include those manufactured by The Procter & Gamble Company of Cincinnati, Ohio as: ALWAYS® Pantiliners with DriWeave® manufactured according to U.S. Pat. Nos. 4,324,246; 4,463,045; and 6,004,893; ALWAYS® Ultrathin Slender Maxi with Wings manufactured according to U.S. Pat. Nos. 4,342,314, 4,463,045, 4,556,146, B1 4,589,876, 4,687,478, 4,950,264, 5,009,653, 5,267,992, and Re. 32,649; ALWAYS® Regular Maxi; ALWAYS® Ultra Maxi with Wings; ALWAYS® Maxi with Wings; ALWAYS® Ultra Long Maxi with Wings; ALWAYS® Long Super Maxi with Wings; ALWAYS® Overnight Maxi with Wings; ALWAYS® Scented Maxi Long Super with Flexi-Wings; ALWAYS® Scented Maxi Regular; ALWAYS® Scented Maxi Ultra with Flexi-Wings; and ALWAYS® Scented Maxi Super Ultra with Flexi-Wings, each aforesaid publication being incorporated by reference herein.

Figure 1:
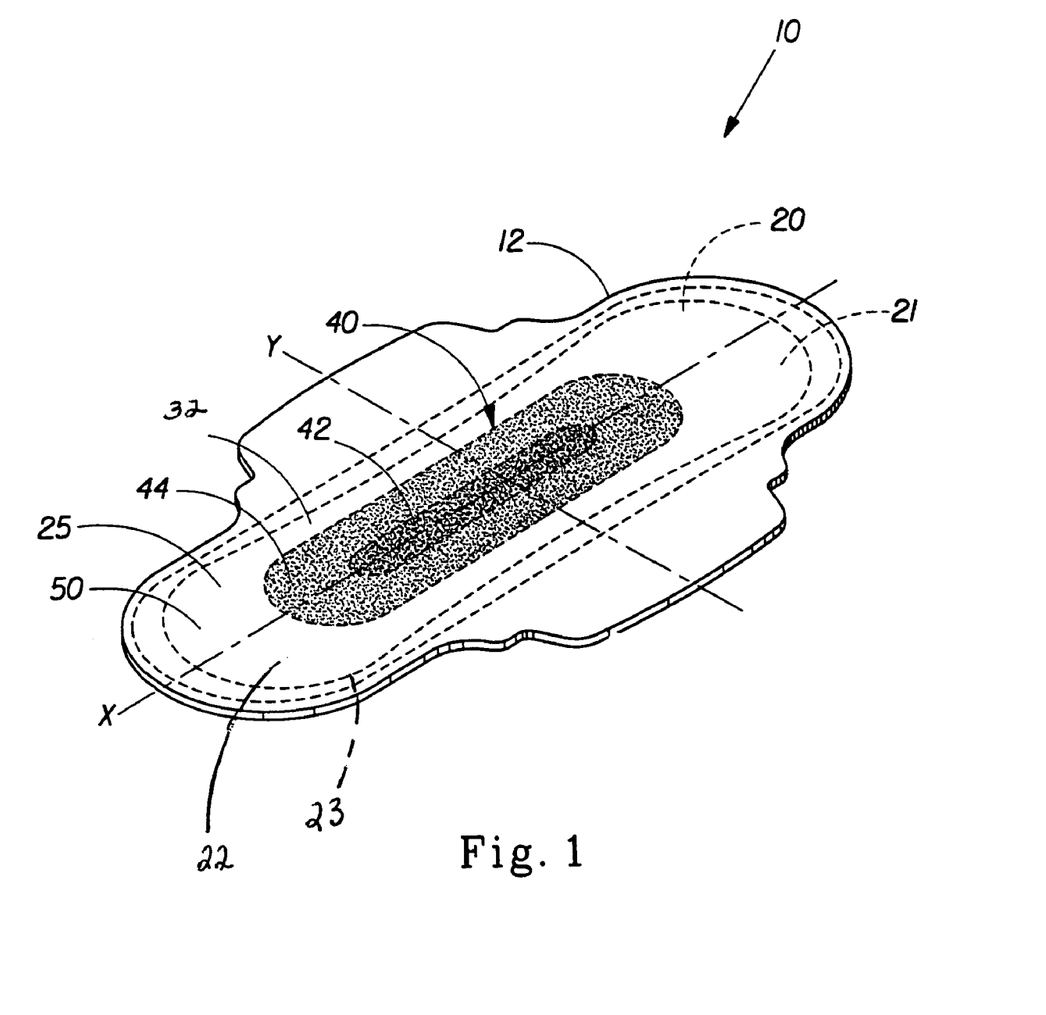
FIG. 1 is a perspective drawing of the absorbent article.

FIG. 1 provides a perspective view of the absorbent article 10. The absorbent article 10 herein has an upper surface 22, a lower surface (not seen), and a periphery 12 comprising a topsheet 25 having a bottom surface (not shown) and a viewing surface 32 positioned opposite to the bottom surface. The viewing surface 32 faces upwardly towards the upper surface 22 of the absorbent article 10. The absorbent article 10 further comprises a backsheet 23 having a garment facing surface (not shown) and a user facing surface positioned oppositely to the garment facing surface, the backsheet 23 being joined to the topsheet 25.

Figure 2:
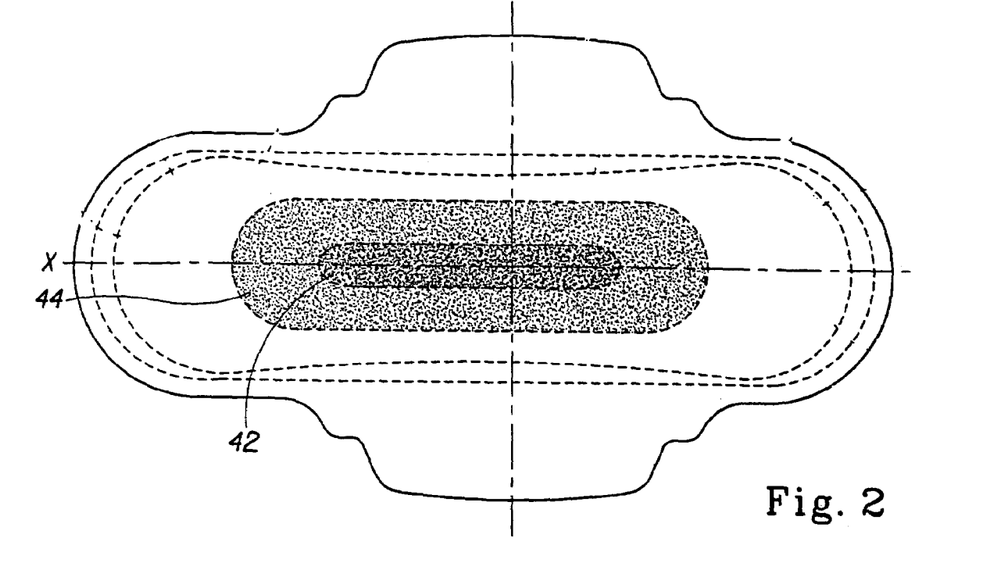
FIG. 2 is a planar view of the absorbent article of FIG. 1.
Figure 3:
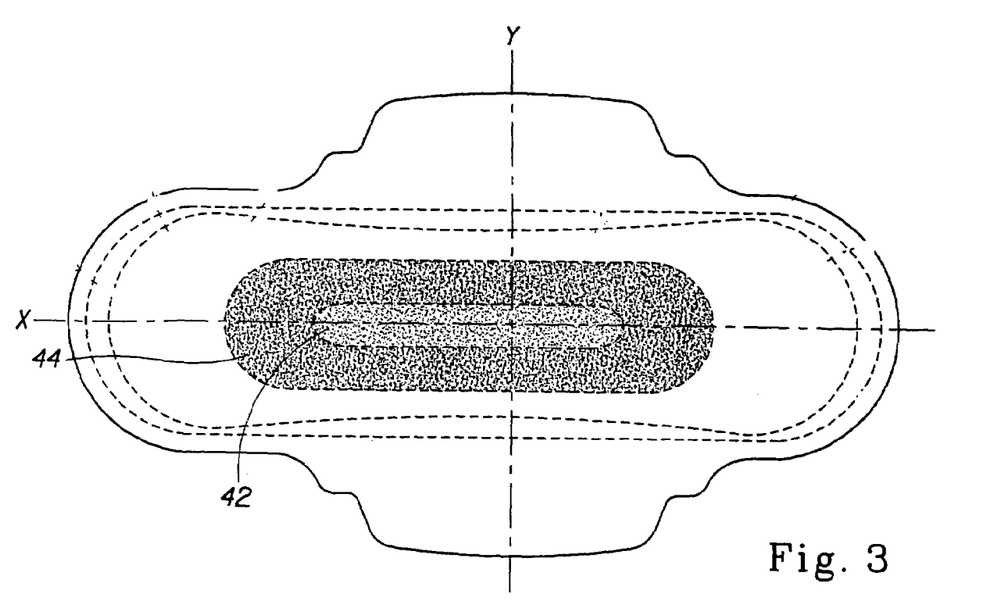
FIG. 3 is a planar view of an alternative embodiment of FIG. 1.

The absorbent article 10 also comprises an absorbent core 20 having a top surface 21 and a bottom surface (not shown) that is positioned opposite to the top surface 21. The absorbent core 20 is positioned between the topsheet 25 and the backsheet 23. In the embodiment shown in FIG. 1 the absorbent article 10 has at least two portions, i.e., a colored portion 40 and a non-colored portion 50. The colored portion 40 and the non-colored portion 50 are viewable from the viewing surface 32 of the topsheet 25. The colored portion 40 has at least two shades, a first shade 42 and a second shade 44. Preferably, but not necessarily, and as is shown in FIG. 1, the first shade 42 is positioned substantially within the second shade 44. The second shade 44 is different, either in lightness, darkness, and/or color, from the first shade 42. The multi-shades operate to create a perception of depth within the absorbent article by a user looking upon the viewing surface 32 of the topsheet 25. Specifically, the lightness and darkness of the shades, whether two or greater than two shades, are configured to create a perception of depth by a user looking upon the viewing surface 32 of the absorbent article 10. As shown in FIG. 2, in one embodiment herein, the first shade 42 of the color may be darker than the second shade 44 of the color. As shown in FIG. 3, alternatively, the first shade 42 may be lighter than the second shade 44.

Figure 4:
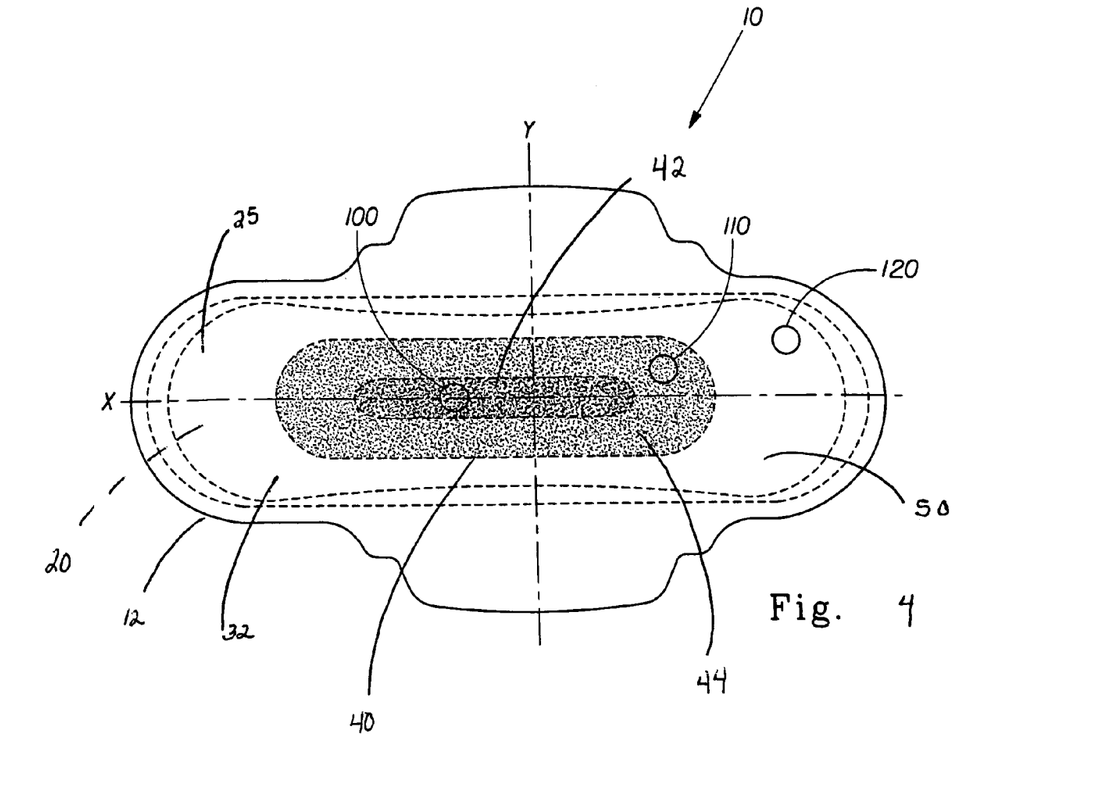
FIG. 4 is a planar view of the proper testing form of the absorbent article of FIG. 1.

Referring to FIG. 4, the color of the first shade 42 and the second shade 44 of the colored portion 40 and the non-colored portion 50 are measured by the reflectance spectrophotometer according to the colors' L*, a*, and b* values. The L*, a*, and b* values are measured from the viewing surface 32 of the topsheet 25 inboard of the absorbent article's periphery 12. The color differences between the colored portion 40 and the non-colored portion 50 are measured at a first point 100, a second point 110, and a third point 120 on the viewing surface 32 of the topsheet 25 inboard of the periphery 12 of the absorbent article 10. Preferably, each one of the points 100, 110, and 120 resides fully within the periphery 12 of the absorbent core 20. For example, the first point 100 is measured within the first shade 42, the second point 110 is measured within the second shade 44, and the third point 120 is measured within the non-colored portion 50 of the absorbent article 10.

The color differences are calculated using the L*, a*, and b* values by the formula $\Delta E=[(L^*_X-L^*_Y)^2+(a^*_X-a^*_Y)^2+(b^*_X-b^*_Y)^2]^{1/2}$. Herein, the 'X' in the equation may represent points 100, 110, or 120. Y may represent points 100, 110, or 120. X and Y should never be the same two points of measurement at the same time. In other words, $X \neq Y$. Where greater than two shades of a color(s) are used, the 'X' and 'Y' values alternately include points of measurement in them also. The key to the $\Delta E$ calculation herein is that the 'X' and 'Y' values should not stem from the same measured point on the viewing surface. In those instances where there is effectively no non-colored portion 50 within the confines of the measurement area, the 'X' values should flow from a point different in spatial relationship to the 'Y' values, but within the confines of the absorbent core periphery 12.

The difference in color ($\Delta E^*$) between the first shade 42 and the second shade 44 should be at least 3.5. The difference in color between the first shade 42 and the non-colored portion 50 is at least 6. The difference in color between the second shade 44 and the non-colored portion 50 is at least 3.5.

Preferably, the size of the non-colored portion 50 ranges from about 5% to about 100% of the viewing surface 32 of the topsheet 25. Also preferably, the first shade 42 of the colored portion 40 is positioned substantially centrally in relation to the second shade 44 of the colored portion 40. However, so long as the shades are in proper spatial relationship to one-another such that the depth perception phenomena is created, any suitable positioning of the shades is foreseeable by one of skill in the art and are therefore acknowledged as suitable alternative embodiments of the invention.

In one embodiment herein, the colored portion 40 may be an insert positioned between the topsheet 25 and the absorbent core 20. In another embodiment, the colored portion 40 forms a part of the topsheet 25. In yet another embodiment herein, the colored portion 40 forms a part of the absorbent core 20 whereby the colored portion 40 is viewable from the viewing surface 32 of the topsheet 25. Alternatively, the colored portion 40 may be a multi-layered insert positioned beneath the topsheet 28.

Any topsheet material that allows the colored portion to be readily seen from the viewing surface 32 of the topsheet 25 is suitable. For example, formed film material, nonwovens, or combinations thereof are suitable.

In an alternative embodiment herein, the absorbent article 10 provides a colored portion 40 wherein the viewing surface 32 of the topsheet 25 is substantially without a non-colored portion 50. By the term 'substantially without a non-colored portion' it is meant herein that color white is less than or equal to 5% of the total surface area of the viewing surface 32. Also alternatively is an embodiment in which a color different from the color of the first shade 42 and the second shade 44 operates as a boundary between the two shades. In other words, this boundary (not shown) rings the outer perimeter of the second shade 44 and separates the second shade 44 from the first shade 42.

Figure 5:
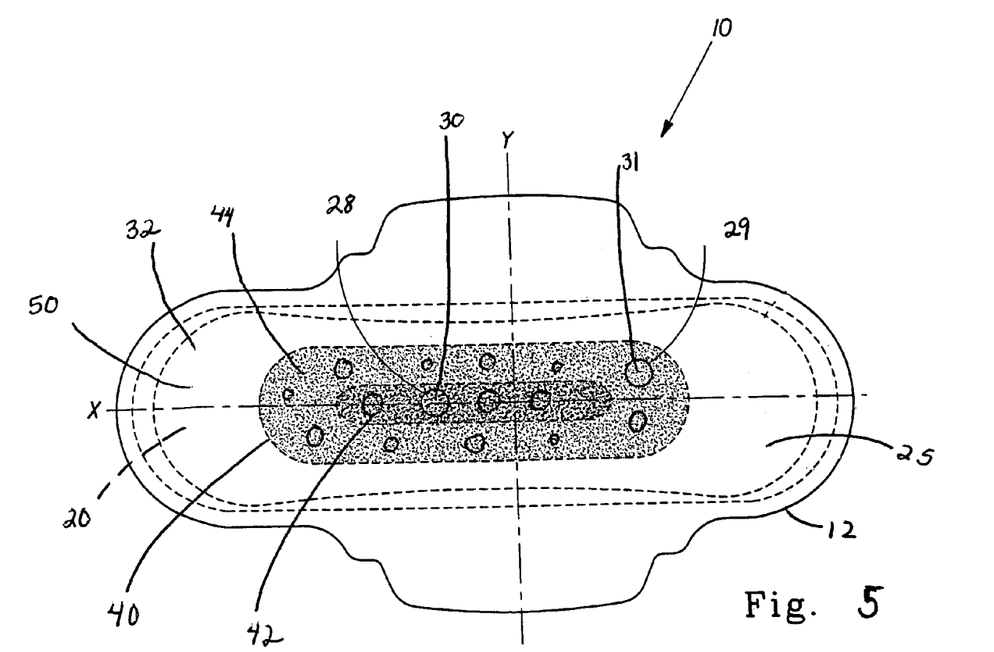
FIG. 5 is a planar view of the proper testing form of the absorbent article of the present invention.

Referring to FIG. 5, the first shade 42 of the colored portion 40 may encompass a graphic 28. The second shade 44 of the colored portion 40 may encompass a graphic 29. The first shade 42 and/or the second shade 44 can encompass one type of graphic 28, 29 or a combination of graphics 28, 29.

The graphics 28, 29 can be any color, shape, or size. The color of the first graphic 28 located within the first shade 42 and the graphic 29 located within the second shade 44 may be substantially similar or the same. The colors are substantially similar if the colors closely resemble each other or if one color has the possibility of being mistaken for the other. A color is the "same" if the color corresponds so closely that is it indistinguishable. For example, however, the color of the first graphic 28 located within the first shade 42 may be different in lightness, darkness, and/or color from the second graphic 29 located within the second shade 44.

The color of each of the graphics 28 within the first shade 42 may be substantially similar or the same color. Likewise, the color of each of the graphics 29 within the second shade 44 may be substantially similar or the same color. In one embodiment, all of the graphics 28 located within the first shade are blue. However, the color of each graphic 28 within the first shade 42 may be different in lightness, darkness, and/or color. Moreover, the color of each graphic 29 within the second shade 44 may be different in lightness, darkness, and/or color. In one embodiment, the graphics 29 within the second shade 44 are a different color. Specifically, half of the graphics 29 are green and the other half of the graphics 29 are yellow.

The graphics 28, 29 can be color coordinated with each other and they can be color coordinated with the first shade 42 and/or the second shade 44. When the graphic 28 which is located within the first shade 42 has a color, the color can be color coordinated with the color of the first shade 42. Likewise, when the graphic 29 which is located within the second shade 44 has a color, the color can be color coordinated with the color of the second shade 44. In addition, the graphic 28 which is located within the first shade 42 can be color coordinated with the second shade 44. Likewise, the graphic 29 which is located within the second shade 44 can color coordinated with the color of the first shade 42.

Figure 6:
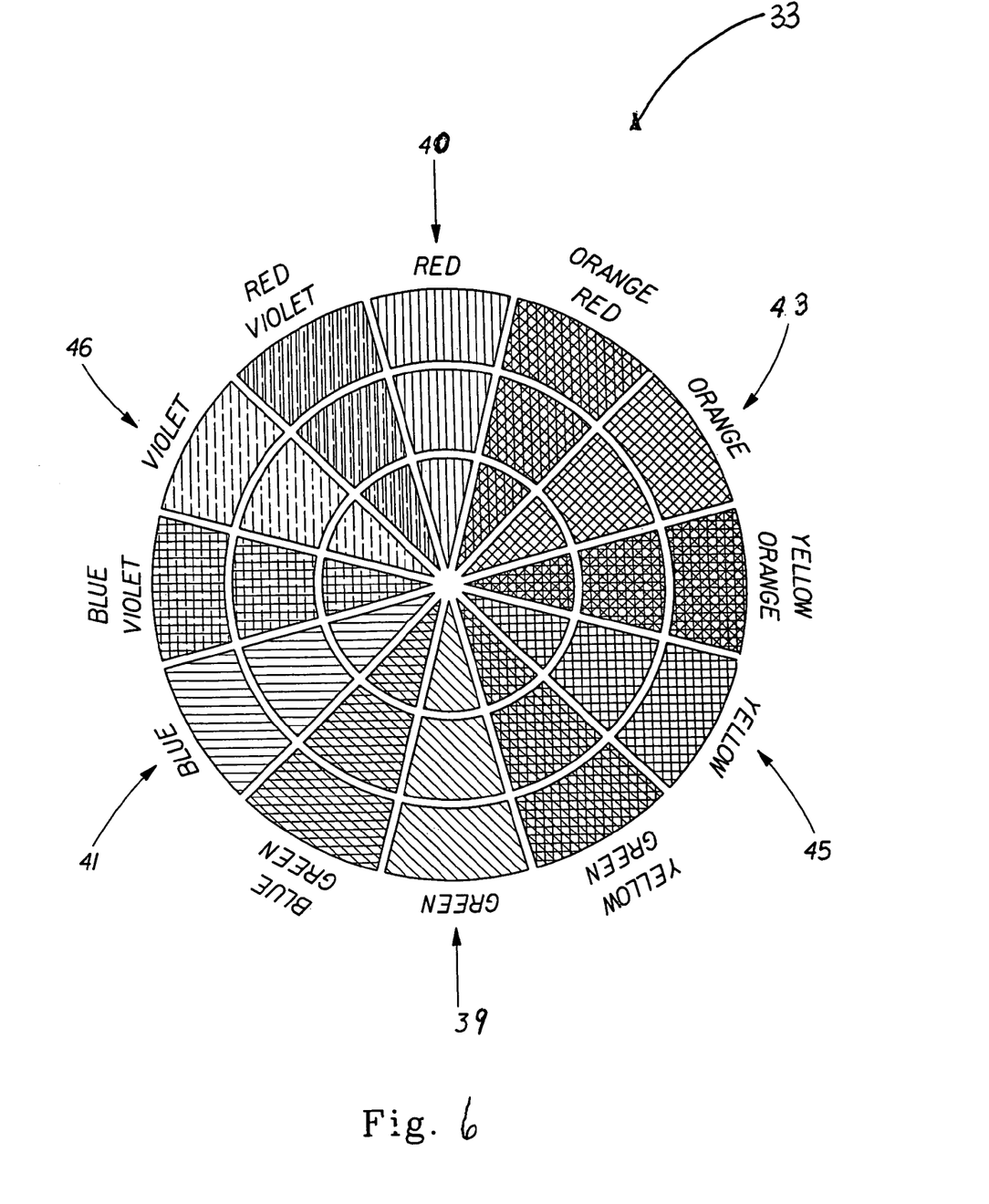
FIG. 6 is a perspective view of the color spectrum.

By color coordinated, is meant the color of at least a portion of the graphic 28, 29 and at least a portion of the first shade 42 and/or the second shade 44 may be complimentary, analogous, warm/cool colors, monochromatic, and/or neutral. Referring to FIG. 6, by complimentary colors, is meant those colors which are directly opposite one other in the color spectrum or wheel 33. For example, blue 41 is the opposite of orange 43. Because blue 41 is the opposite of orange 43, gold, rust, and brown compliment shades of blue 41. By analogous colors, is meant those colors which are next to each other on the color wheel. For example, blue 41 could be color coordinated with green 39. By warm and cool colors, is meant families of analogous colors. Warm colors are colors such as red 40, orange 43, and yellow 45. Cool colors are colors such as green 39, blue 41, and violet 46. Warm and cool colors may be mixed together. For example, graphic 28 which has two warm colors located on graphic 28 may be selected to match with one cool color on the graphic 29. In another example, graphic 28 which is located within the first shade 42 has two cool colors which may be color coordinated with a graphic 29 located within the second shade 44 having a warm color. By monochromatic, is meant all one color, but different shades, tones, or tints. By neutral, is meant shades of white, black, gray, or beige.

Referring again to FIG. 5, the graphic 28 within the first shade 42 and the graphic 29 within the second shade 44 of the colored portion 40 and the non-colored portion 50 are measured by the reflectance spectrophotometer according to the colors' L*, a*, and b* values. The L*, a*, and b* values are measured from the viewing surface 32 of the topsheet 25 inboard of the absorbent article's periphery 12. The color differences between the graphic 28 within the first shade 42 and the graphic 29 within the second shade 44 are measured at a first point 30 and a second point 31 on the viewing surface 32 of the topsheet 25 inboard of the periphery 12 of the absorbent article 10. Preferably, each one of the points 30 and 31 resides fully within the periphery 12 of the absorbent core 20. For example, the first point 30 is measured within the first graphic 28 which is located within the first shade 42 and the second point 31 is measured within the second graphic 29 which is located within the second shade 44.

The color differences are calculated using the L*, a*, and b* values by the formula $\Delta E = [(L^*_X - L^*_Y)_2 + (a^*_X - a^*_Y)^2 + (b^*_X - b^*_Y)^2]^{1/2}$. Herein, the 'X' in the equation may represent points 30 or 31. Y may represent points 30 or 31. X and Y should never be the same two points of measurement at the same time. In other words, X≠Y. Where greater than two shades of a color(s) are used, the 'X' and 'Y' values alternately include points of measurement in them also. The key to the ΔE calculation herein is that the 'X' and 'Y' values should not stem from the same measured point on the viewing surface. In those instances where there is effectively no non-colored portion 50 within the confines of the measurement area, the 'X' values should flow from a point different in spatial relationship to the 'Y' values, but within the confines of the absorbent core periphery 12.

The difference in color (ΔE*) between the first graphic 28 which is located within the first shade 42 and the second graphic 29 which is located within the second shade 44 should be at least 3.5. The difference in color between the first graphic 28 within the first shade 42 and the non-colored portion 50 is at least 6. The difference in color between the second graphic 29 within the second shade 44 and the non-colored portion 50 is at least 3.5.

The graphics 28, 29 can be any shape such as rectangular, square, elliptical, polygonal, triangular, etc. Other examples of possible shapes are flowers, circles, trapezoids, cones, alphabet letters, and mixtures thereof. In one embodiment, the graphic 28 which is located within the first shade 42 is shaped like a flower. Not only can graphic 28 and graphic 29 be different, the graphic 28 and graphic 29 can be the same or substantially the same.

The graphic 28 within the first shade 42 may be formed to have essentially identical size as compared to the graphics 29 which are located within the second shade 44. Alternatively, graphics 29 within the second shade 44 may be formed to have various sizes as compared to graphics 28 located within the first shade 42.

Each graphic 28 within the first shade 42 may be formed to have essentially identical size as compared to other graphics 28 within the first shade 42. Likewise, each graphic 29 located within the second shade 44 may be formed to have essentially identical size as compared to other graphics 29 within the second shade 44. Alternatively, graphics 28 within the first shade 42 may be formed to have various sizes as compared to other graphics 28 within the first shade 42. Likewise, alternatively, graphics 29 within the second shade 44 may be formed to have various sizes as compared to other graphics 29 within the second shade 44.

The graphics 28, 29 within the first shade 42 and/or the second shade 44 may be arranged randomly or in a pattern. For example, the graphics 28, 29 can be arranged to form any three-dimensional geometric pattern known including but not limited to flowers, ovals, circles, rectangles, trapezoids, triangles, cones, alphabet letters, and mixtures thereof.

The graphic 28 may encompass the entire area of the first shade 42 or may encompass part of the first shade 42. Likewise, the graphic 29 may encompass the entire second shade 44 or may encompass part of the second shade 44. For example, graphic 28 which is located within the first shade 42 may encompass 50% of the first shade 42 and graphic 29 which is located within the second shade 44 may encompass 90% of the second shade 44.

C. Analytical Methodology—Hunter Color

Figure 7:
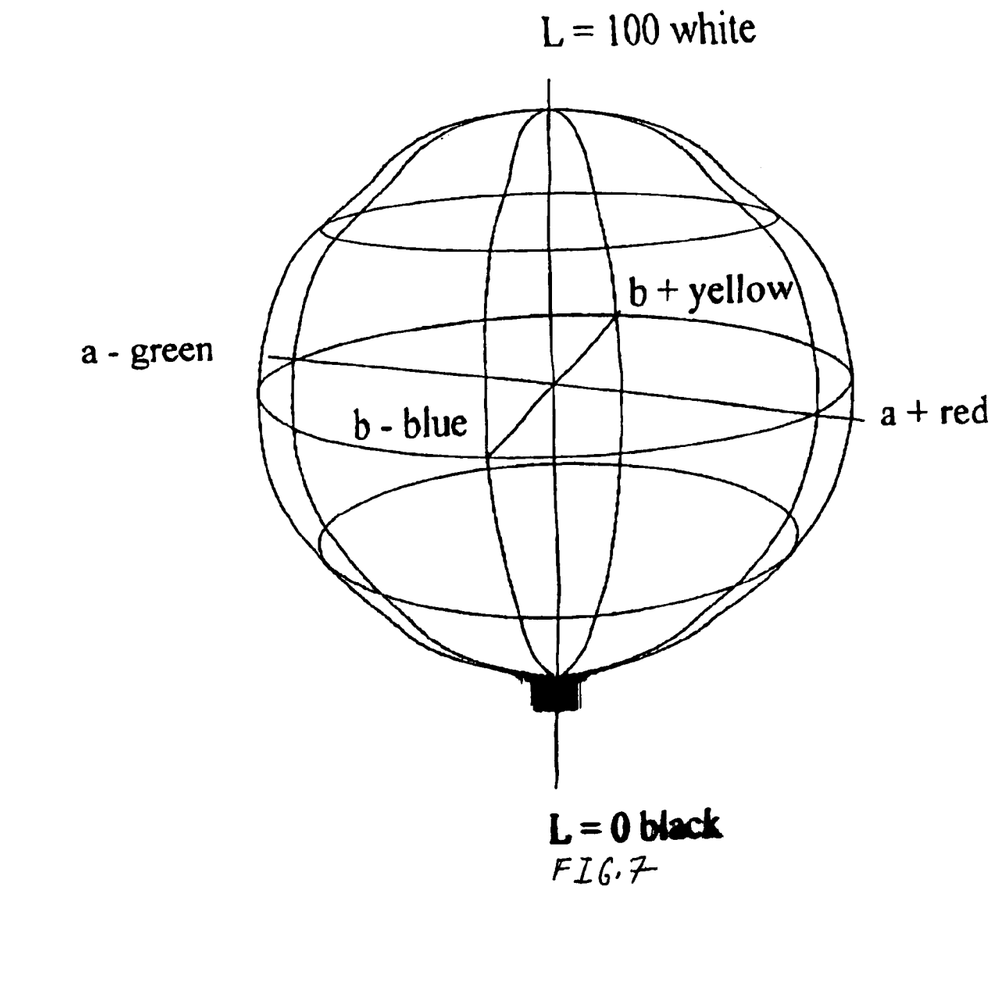
FIG. 7 is an illustration of the Commission Internationale de l'Eclairage L*a*b* color space.

Referring to FIG. 7, the color scale values, utilized herein to define the darkness/lightness of the materials of the absorbent articles according to the present invention, is the widely accepted CIE LAB scale. Measurements are made with a Hunter Color reflectance meter. A complete technical description of the system can be found in an article by R. S. Hunter, 'photoelectric color difference Meter', Journal of the Optical Society of America, Vol. 48, pp. 985-95, 1958. Devices specially designed for the measurement of color on the Hunter scales are described in U.S. Pat. No. 3,003,388 to Hunter et al., issued Oct. 10, 1961. In general, Hunter Color "L" scale values are units of light reflectance measurement, and the higher the value is, the lighter the color is since a lighter colored material reflects more light. In particular, in the Hunter Color system the "L" scale contains 100 equal units of division. Absolute black is at the bottom of the scale (L=0) and absolute white is at the top of the scale (L=100). Thus, in measuring Hunter Color values of the materials used in the absorbent articles according to the present invention, the lower the "L" scale value, the darker the material. The absorbent articles herein, and hence the materials of which the absorbent articles are made of, might be of any color provided that the L Hunter value defined herein is met.

Colors can be measured according to an internationally recognized 3D solid diagram of colors where all colors that are perceived by the human eye are converted into a numerical code. The CIE LAB system is similar to Hunter L, a, b an is based on three dimensions, specifically L*, a*, and b*.

When a color is defined according to this system L* represents lightness (0=black, 100=white), a* and b* independently each represent a two color axis, a* representing the axis red/green (+a=red, −a=green), while b* represents the axis yellow/blue (+b=yellow, −b=blue). FIG. 7 shows the proper representation of the L, a, and b axes.

A color may be identified by a unique ΔE value (i.e., different in color from some standard or reference), which is mathematically expressed by the equation:

$$\Delta E^* = [(L^*_X - L^*_Y)^2 + (a^*_X - a^*_Y)^2 + (b^*_X - b^*_Y)^2]^{1/2}$$

'X' represents the standard or reference sample which may either be a 'white' sample or a 'colored' sample, e.g., one colored shade may be compared to another colored shade.

It is to be understood that the tristimulus color values and $\Delta E^*$ considered herein are those measured on the materials of interest (e.g., the colored and non-colored portions on the viewing surface of the topsheet disclosed herein).

The Hunter color meter quantitatively determines the amount (percent) of incident light reflected from a sample onto a detector. The instrument is also capable of analyzing the spectral content of the reflected light (e.g., how much green is in the samples). The Hunter color meter is configured to yield 3 values ($L^*$, $a^*$, $b^*$ and $\Delta E^*$ which is total color). The $L^*$ value is simple the percent of the incident (source) light that is reflected off a target sample and onto the detector. A shiny white sample will yield an $L^*$ value near 100 while a dull black sample will yield an $L^*$ value of about 0. The $a^*$ and $b^*$ value contains spectral information for the sample. Positive $a^*$ value indicates the amount of green in the sample.

Testing is conducted using a Lab Scan XE 45/0 geometry instrument to measure the different shaded options for the visual signal zone. The Hunter Color in CIE lab scale 2° C. was measured on each pad in 3 portions. A 0.7 inch diameter port was used having a 0.50 inch area view, which was the largest size able to measure each zone discretely; i.e., this 0.5 inch area view is important for the purposes these measurements and should not be made smaller than the 0.5 inch area view prescribed. The instrument was calibrated using standard white and black tiles supplied by the instrument manufacturer.

A. Color Zone Measurement for Pad Topsheet Appearance

For measuring the $L^*$, $a^*$, and $b^*$ values for the invention herein, a standard, industry-recognized procedure is used. The topsheet color is measured using a reflectance spectrophotometer in accordance with method ASTM E 1164-94, "Standard Practice for Obtaining Spectrophotometric Data for Object-Color Evaluation". This standard method is followed but specific instrument settings and sampling procedure are given here for clarity. Sample color is reported in terms of the CIE 1976 color coordinate standard as specified in ASTM E 1164-94 and ASTM D2264-93, section 6.2. This consists of three values; $L^*$ which measures sample "lightness", $a^*$ which measures redness or greenness, and $b^*$ which measures yellowness or blueness.

| Apparatus | |
|---|---|
| Reflectance Spectrophotometer | 45°/0° Hunter Labscan XE, or equivalent HunterLab Headquarters, 11491 Sunset Hills Road, Reston VA 20190-5280 Tel: 703-471-6870 Fax: 703-471-4237 http://www.hunterlab.com. |
| Standard plate | Standard Hunter White Tile Source: Hunter Color. |

Equipment Preparation
1. Assure that the Spectrophotometer is configured as follows:

| | |
|---|---|
| Illumination | Type C |
| Standard Observer | 2° |
| Geometry | 45/0° Measurement angle |
| Port Diameter | 0.70 inch |
| Viewing area | 0.50 inch (and no smaller) |
| UV Filter: | Nominal |

2. Calibrate the spectrophotometer using standard black and white tiles supplied with the instrument according to manufacturer's instructions before beginning any testing.

Sample Preparation
1. Unwrap, unfolded and lay the product or pad samples flat without touching or altering the color of the body facing surface.
2. Areas on the body-facing surface of the product should be selected for measurement and must include the following:
    The non-colored portion of the topsheet.
    The colored portion of the topsheet; including the two or more shaded portions.
    Any other portions of the topsheet above the absorbent core having a visibly or measurably different color from the first shaded zone. Embossed channels and folds should not be included in zones of measurement as they may skew the proper results. Measurements should not be made overlapping the border of two shaded portions.

Test Procedure
1. Operate the Hunter Colorimeter according to the instrument manufacturer's instructions.
2. Pads should be measured laying flat over the 0.70 inch aperture on the instrument. A white tile should be placed behind the pad.
3. The pad should be placed with its long direction perpendicular to the instrument.
4. Measure the same zones selected above for at least 3 replicate samples.

Calculation Reporting
1. Ensure that the reported results are really CIE $L^*$,$a^*$,$b^*$.
2. Record the $L^*$,$a^*$,$b^*$ values to the nearest 0.1 units.
3. Take the average $L^*$, $a^*$, $b^*$ for each zone measured.
4. Calculate $\Delta E^*$ between different shaded portions and $\Delta E^*$ between each shaded portion and the non-colored portion where the non-colored portion exists.

Human Sensitivity to Light

The human sensitivity threshold for the lightness of a dark green color is a $\Delta E^*$ of about 1.0. For a dark green color, if only the $a^*$ and $b^*$ change, human sensitivity is a $\Delta E^*$ of 2.4. In the context of an absorbent article herein (e.g., a sanitary napkin) it is highly likely that many people would not see a color difference if the $\Delta E^*$ is less than 2. This sensitivity is described in the following reference: "The Measurement of Appearance", by Hunter and Harold, 2nd edition, 1987, (ISBN 0-471-83006-2).

Chapter 4 of Hunter's book describes human color sensing and chapter 9 is about color scales. By making side-by side comparison, humans can differentiate up to 5 to 10 million different colors. In the 1940s, a researcher named MacAdam did human chromaticity discrimination experiments. He found the thresholds of sensitivity and showed these depend on the color. Later work by Brown and MacAdam came up with a logarithmic lightness dimension scale for human sensitivity to go with the earlier color scale. Based on the reduction to practice of the invention, experimentation and the foregoing work by Brown and MacAdam, it has been found herein that a $\Delta E \geq 3.5$ is the preferred range to effect proper differentiation between the shades that provides the proper appearance of depth. However, where the $\Delta E$ is as small as about 1 and still operates to provide a perception of depth between the shades, this $\Delta E$ is also contemplated and included herein. An example where $\Delta E$ may be between at last two shades of one or more colors may be found in an alternative embodiment that provides a multi-color and/or shade gradient of a color across the viewing surface of the absorbent article.

B. Results

CHART I

| Sample Number | Topsheet Type | Colored Options | $\Delta E^*_{23}$ | $\Delta E^*_{12}$ | $\Delta E^*_{13}$ |
|---|---|---|---|---|---|
| 1 | Formed Film | Two-tone inner/outer color | 6.10 | 10.83 | 16.86 |
| 2 | Formed Film | One-tone color | 0.25 | 8.60 | 8.80 |
| 3 | Non-woven | One-tone color | 0.22 | 10.63 | 10.81 |
| 4 | Non-woven | Two-tone inner/outer color | 5.98 | 11.03 | 16.92 |
| 5 | Formed Film | Two-tone light outer color/inner dark color | 10.01 | 2.88 | 12.80 |
| 6 | Formed Film | Two-tone medium outer color/inner dark color | 7.51 | 6.37 | 13.61 |
| 7 | Formed Film | Two-tone darker outer color/inner dark color | 5.60 | 19.16 | 14.22 |
| 8 | Formed Film | Two-tone (secondary topsheet colored outer color)/(core colored dark color) | 4.58 | 6.00 | 8.06 |
| 9 | Formed Film | One-tone outer color | 0.21 | 8.90 | 8.84 |

As has been noted previously, the difference in color between the first shade and the second shade should be at least 3.5. Likewise, the difference in color between the first graphic and the second graphic can also be at least 3.5. The difference in color between the first shade and the non-colored portion is at least 6. Likewise, the difference in color between the first graphic and the non-colored portion is at least 6. The difference in color between the second shade and the non-colored portion is at least 3.5. Likewise, the difference in color between the second graphic and the non-colored portion is at least 3.5. Through experimentation and reduction to practice of the invention, it has been determined that the preferred creation of depth perception happens at about and above these set parameters. For products substantially not having a non-colored portion within the measurement zone (i.e., a gradient or fully colored product), the above criteria for the shaded portions (i.e., $\Delta E^* \geq 3.5$) remains the preferred standard.

Chart I above clearly shows the $\Delta E^*$s obtained between multi-tone (e.g., two tone) and single tone signals. Formed films and nonwovens useful for the invention herein are those which will allow the sufficient penetration of light therethrough such that the shaded portions may be clearly discerned and such that such discernment produces the depth perception effect. The color may be any suitable color fitting within the parameters herein for $\Delta E^*$ between colored portions and non-colored portion (where it exists). For example, the colors green, blue, red, yellow, orange, purple and any other color within the color spectrum are suitable for the purposes described herein.

Sample Nos. 1 and 2 are clearly distinct in their $\Delta E^*23$. Specifically, the $\Delta E^*_{23}$ (which is 6.10) is greater than 3.5. This $\Delta E_{23}$ indicates that there is a perceptible difference in color or lightness/darkness between the two points of measurement; i.e., between the second shaded portion and the non-colored (or white) portion (see FIG. 2 and FIG. 3). As noted above for human perception, Sample No. 2's $\Delta E^*23$ of 0.25 would not be perceptible to the human eye. This indicates that the signal is only a one or single tone signal (i.e., color portion).

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having an upper surface, a lower surface and a periphery, comprising:
    a topsheet having a bottom surface and a viewing surface positioned opposite to the bottom surface, the viewing surface facing upwardly towards the upper surface of the absorbent article;
    a backsheet having a garment facing surface and a user facing positioned oppositely to the garment facing surface, the backsheet being joined to the topsheet;
    an absorbent core having a top surface and a bottom surface positioned opposite to the top surface, the absorbent core being positioned between the topsheet and the backsheet; and
    the absorbent core having a colored portion printed thereon, the colored portion being viewable from the viewing surface of the topsheet, the colored portion having a first shade and a second shade, wherein the first shade comprises a first graphic, the first shade being positioned substantially within the second shade, the second shade being different from the first shade, the shades operating to create a perception of depth within the absorbent article by a user looking upon the viewing surface of the topsheet.

2. The absorbent article of claim 1 wherein said second shade comprises a second graphic.

3. The absorbent article of claim 1 wherein said first shade comprises a first graphic and said second shade comprises a second graphic.

4. The absorbent article of claim 3 wherein said first graphic comprises a different shape than said second graphic.

5. The absorbent article of claim 3 wherein said first graphic has a first color and a second graphic has a second color.

6. The absorbent article of claim 3 wherein the color of the first graphic, the second graphic, the color of the first shade, the color of the second shade of the colored portion, and the non-colored portion are measured by the Hunter Reflectance Meter test according to the colors' L, a, and b values, the L, a, and b values being measured from the viewing surface of the topsheet inboard of the absorbent article's periphery.

7. The absorbent article of claim 6 wherein the color differences between the first graphic, the second graphic, and the non-colored portion are measured at a first point, a second point, and a third point on the viewing surface of the topsheet inboard of the periphery of the absorbent article, the first point being measured within the first graphic, the second point being measured within the second graphic, and the third point being measured within the non-colored portion of the absorbent article, the color differences being calculated using the L, a, and b values by the formula $$\Delta E = [(L^*_x - L^*_y)^2 + (a^*_x - a^*_y)^2 + (b^*_x - b^*_y)^2]^{1/2}$$

8. The absorbent article of claim 7 wherein the difference in color between the first graphic and the second graphic is at least 3.5.

9. The absorbent article of claim 7 wherein the difference in color between the first graphic and the non-colored portion is at least 6.

10. The absorbent article of claim 7 wherein the difference in color between the second shade and the non-colored portion is at least 3.5.

11. The absorbent article of claim 1 wherein the size of the colored portion ranges from about 5% to about 98% of the viewing surface of the topsheet.

12. An absorbent article having an upper surface, a lower surface and a periphery, comprising:
  a topsheet having a bottom surface and a viewing surface positioned opposite to the bottom surface, the viewing surface facing upwardly towards the upper surface of the absorbent article;
  a backsheet having a garment facing surface and a user facing positioned oppositely to the garment facing surface, the backsheet being joined to the topsheet;
  an absorbent core having a top surface and a bottom surface positioned opposite to the top surface, the absorbent core being positioned between the topsheet and the backsheet; and
  the absorbent core having a colored portion printed thereon, the colored portion being viewable from the viewing surface of the topsheet, the colored portion having a first shade and a second shade, the first shade being positioned substantially within the second shade, wherein the first shade of the color is darker than the second shade of the color, and wherein the first shade comprises a first graphic, the shades operating to create a perception of depth within the absorbent article by a user looking upon the viewing surface of the topsheet.

13. The absorbent article of claim 12 wherein the first graphic comprises a color.

14. The absorbent article of claim 13 wherein said first graphic is a flower.

15. An absorbent article having an upper surface, a lower surface and a periphery, comprising:
  a topsheet having a bottom surface and a viewing surface positioned opposite to the bottom surface, the viewing surface facing upwardly towards the upper surface of the absorbent article;
  a backsheet having a garment facing surface and a user facing positioned oppositely to the garment facing surface, the backsheet being joined to the topsheet;
  an absorbent core having a top surface and a bottom surface positioned opposite to the top surface, the absorbent core being positioned between the topsheet and the backsheet; and
  the absorbent core having a colored portion all printed thereon, the colored portion being viewable from the viewing surface of the topsheet, the colored portion having a first shade and a second shade, the first shade being positioned substantially within the second shade, the second shade being darker than the first shade, said first shade comprises a first graphic, the shades operating to create a perception of depth within the absorbent article by a user looking upon the viewing surface of the topsheet.

* * * * *